United States Patent [19]

Van Seters et al.

[11] 4,453,025

[45] Jun. 5, 1984

[54] PROCESS FOR THE PREPARATION OF 3,5-XYLENOL

[75] Inventors: Antonius J. C. Van Seters; Freddy Wattimena, both of Amsterdam, Netherlands

[73] Assignee: Shell Oil Company, Houston, Tex.

[21] Appl. No.: 443,990

[22] Filed: Nov. 23, 1982

[30] Foreign Application Priority Data

Dec. 2, 1981 [GB] United Kingdom ............... 8136372

[51] Int. Cl.$^3$ ............................................. C07C 37/06
[52] U.S. Cl. ................................... 568/799; 568/772; 568/806
[58] Field of Search ................. 568/799, 772, 806

[56] References Cited

U.S. PATENT DOCUMENTS

| | | | |
|---|---|---|---|
| 2,369,196 | 2/1945 | Williams et al. | 568/806 |
| 3,514,492 | 5/1970 | Juguin et al. | 568/799 |
| 3,801,651 | 4/1974 | Adolphen et al. | 568/799 |
| 4,086,282 | 4/1978 | Wattimens | 568/799 |

FOREIGN PATENT DOCUMENTS

| | | | |
|---|---|---|---|
| 1543878 | 1/1970 | Fed. Rep. of Germany | 568/806 |
| 1190802 | 7/1970 | United Kingdom | 568/806 |
| 1190803 | 7/1970 | United Kingdom | 568/806 |
| 1190804 | 7/1970 | United Kingdom | 568/806 |

*Primary Examiner*—Werren B. Lone

[57] ABSTRACT

Isophorone is converted to 3,5-xylenol in the vapor phase in the presence of a heterogeneous catalyst comprising a particular combination of multiple rare earth metals on an alumina support or one or more rare earth metals in combination with one or more transition metals and/or one or more alkali or alkaline earth metals. Particularly good results are obtained with a catalyst comprising a naturally-occurring mixture of rare earth metals known as didymium in combination with potassium and cobalt promoters.

26 Claims, No Drawings

PROCESS FOR THE PREPARATION OF 3,5-XYLENOL

BACKGROUND OF THE INVENTION

This invention relates to a process for the preparation of 3,5-xylenol from 3,5,5-trimethylcyclohexene-2-one (isophorone).

3,5-xylenol is recognized to be useful as a disinfectant and as a starting material for the preparation of resins, vitamin E, and other compounds, including dyes, agricultural, pharmaceutical and aroma chemicals.

It is known that isophorone can be converted at elevated temperatures to 3,5-xylenol (also known as 3,5-dimethylphenol and as 1,3-dimethyl-5-hydroxybenzene) without the use of a catalyst. However, for good yields of the desired product it is necessary to employ a catalyst, which may be either homogeneous (for example, a halogen or organic halogen compound as described in U.S. Pat. No. 4,086,282) or heterogeneous (for example, certain supported metals or metal compounds as described in U.S. Pat. No. 2,369,197 or Great Britain patent specification Nos. 1,197,803 and 1,451,570).

In principal, a heterogeneous catalyst is typically preferred for the reaction, in order to eliminate problems of catalyst separation from the product 3,5-xylenol. However, use of known heterogeneous catalysts fails to result in the desired selectivities and/or conversions and/or reaction rates. As in all catalytic processes, conversion, selectivity and rate are important from the standpoint of utilization of starting material and catalyst. It is further of particular importance to maximize selectivity and conversion in this process because separation of by-products and isophorone from 3,5-xylenol is difficult. Still further and perhaps most importantly, selectivity is a critical aspect of this conversion because the formation of by-products is accompanied by deactivation of heterogeneous catalysts through buildup of solid carbonaceous deposits, shortening effective catalyst life and dictating frequent regeneration.

Commercially acceptable levels of conversion have been achieved using heterogeneous catalysts comprising cobalt and molybdenum, as are described in the aforementioned Great Britain patent specification No. 1,451,570. However, the selectivity of such catalyst is less than would be desired.

With regard to particular features of the present invention relating to certain rare earth metals as components of catalysts for the conversion of isophorone to 3,5-xylenol, U.S. Pat. No. 2,369,197 makes mention of a cerium containing catalyst, but expresses preference for other metals (i.e., iron, cobalt, and/or chromium). With regard to other features of the invention relating to alkali or alkaline earth metals and to transition metals as catalyst components, U.S. Pat. No. 2,369,197 and Great Britain No. 1,451,570 list certain of such metals, although not in combination with rare earth metals.

SUMMARY OF THE INVENTION

It has now been found that in the process for preparation of 3,5-xylenol which comprises contacting isophorone with a heterogeneous catalyst at elevated temperature, significant improvement in overall conversion, rate and selectivity of 3,5-xylenol is realized by employing certain catalysts comprising rare earth metals.

In one specific aspect, the invention is directed to a process in which the catalyst comprises didymium, a particular combination of multiple elements of the rare earth metal series supported on an alumina carrier.

In another specific aspect, the invention is directed to a process in which the catalyst comprises a combination of one or more rare earth metals with one or more reaction promoters, again supported on an alumina carrier. Suitable for use as a promoter are one or more alkali or alkaline earth metals and/or one or more transition metals selected from Group IB, VIB, or VIII of the Periodic Table.

DESCRIPTION OF THE PREFERRED EMBODIMENT

The present invention is directed to a process for preparation of 3,5-xylenol, with comprises contacting isophorone with particular heterogeneous catalysts. Apart from these catalysts, conditions and procedures known to the art for the catalytic conversion of isophorone to 3,5-xylenol are generally suitable for purposes of this invention. The relevant teachings of U.S. Pat. No. 2,369,197 are incorporated herein for description of such conditions and procedures.

Certain preferences may still be expressed, however, for purposes of processing under this invention. For instance, the invention is preferably carried out at a temperature in the range from about 525° C. to 625° C., which is within that recommended in U.S. Pat. No. 2,369,197. This preferred range is about 25° C. below that specified in Great Britain No. 1,451,570. By maintaining high activity at a lower temperature, the catalyst in the process of the invention is less subject to fouling by carbon deposits and thus realizes a longer life between regenerations. At temperatures within the preferred range, the reaction is accomplished with isophorone reactant in the vapor phase. Process pressure is suitably atmospheric although higher or lower pressures may be employed so long as a vapor phase reaction is maintained. Isophorone may be mixed with a suitable diluent, for example, hydrogen or steam, to aid in reducing carbon deposits on the catalyst. A process in which isophorone vapor is continuously passed through a contained bed of the solid catalyst is preferred, particularly one in which space velocity of the reactant is in the range from about 0.25 to 1.5 kilograms of isophorone per liter of catalyst per hour (kg/1/hr). Most preferably, the space velocity of reactant is in the range from about 0.5 to about 1.0 kg/1/hr. Very advantageously, preferred space velocity for this invention is higher than that suitably utilized in the process of Great Britain No. 1,451,570, typically by a factor of 2 to 5. The process results in a reaction mixture from which minor amounts of unreacted isophorone and by-products such as toluene, xylene, mesitylene, m-cresol, dihydroisophorone, and trimethylphenol may be removed by conventional means (e.g., as described in U.S. Pat. No. 2,369,197 and Great Britain No. 1,197,803) to produce a high quality 3,5-xylenol product.

With regard to catalysts suitable for purposes of this invention, consideration is necessarily given to both the carrier and to catalytically active metals (or metal compounds) supported thereon. Further consideration is given to a preference for a catalyst having a specific surface area not exceeding about 1.0 square meter per gram ($M^2/g$), particularly for a catalyst having a specific surface area below about 0.5 $M^2/g$.

The carrier is based on and comprises in major part alumina ($Al_2O_3$). Minor amounts of other known carrier materials, e.g., silica or magnesia, may also suitably be present in the carrier. Preferably, however, substantially pure alumina is used, particularly alpha-alumina. The preferences with respect to specific surface area of the catalyst can be observed either by selection of the appropriate grade of alumina or by calcination of higher surface area alumina, particularly after impregnation with active metal(s), at high temperature (e.g. 1100° C.) to reduce surface area.

Supported on the carrier for purposes of one aspect of the invention is a naturally-occurring mixture of rare earth metals known as didymium (Di). Although in the past the term has on occasion been used to mean a mixture of neodymium and praseodymium, didymium is now used, both generally in the art (Kirk-Othmer, Encyclopedia of Chemical Technology (1968), Vol. 17, p. 147) and specifically in describing this invention, to represent mixtures comprising various elements of the lanthanum series (elements having atomic number from 57 to 71, inclusive), with the exception of cerium, in their natural ratio of abundance. The suitability of such a mixture of elements for purposes of the invention is of substantial advantage, since the separation of an individual element of the lanthanum series from the mixture in which they are commonly found is particularly difficult.

Practice may also be made under the invention employing a catalyst which combines on the alumina carrier one or more rare earth metals with one or more alkali or alkaline earth metals and/or one or transition metals function to promote the catalytic action of the rare earth metal and afford still further improvement in process selectivity.

Under this aspect of the invention, suitable rare earth metals include those of the lanthanum series, as well as the element scandium of atomic number 21 and the element yttrium of atomic number 39. A catalyst comprising one or more metals selected from the group consisting of scandium, yttrium, lanthanum, cerium, praseodymium, neodymium, and samarium is preferred, and a catalyst comprising one or more metals selected from the group consisting of scandium, yttrium, lanthanum, and cerium is considered most preferred. Suitable alkali and alkaline earth metals are lithium, sodium, potassium, rubidium, cesium, magnesium, calcium, strontium and barium. Potassium is particularly preferred. Suitable transition metals are copper, silver and gold (Group IB of the Periodic Table); chromium, molybdenum, and tungsten (Group VIB); and iron, cobalt, nickel, ruthenium, rhodium, palladium, osmium, iridium, and platinum (Group VIII). The transition metal component of the catalyst preferably comprises one or more elements selected from the group consisting of copper, silver, cobalt and molybdenum. Cobalt is particularly preferred. The catalyst may combine one or more of the rare earth metals and one or more of the alkali or alkaline earth metals (omitting any significant amount of the transition metal), or one or more of the rare earth metals and one or more of the transition metals (omitting any significant amount of the alkali or alkaline earth metal. However, preference is observed for catalysts combining one or more representatives from each of the three groups.

It is to be understood that when reference is made herein to a metal as a catalyst component not only the metal per se but also compounds thereof, for instance, the oxides, are also contemplated.

In any embodiment of the invention the quantity of rare earth metal is not critical, although it may be practically limited by the absorption capacity of the carrier. It is typical for the catalyst to very suitably contain between about 0.5 and 20 percent by weight (%w) of the specified one or more rare earth metals (or compounds thereof, calculated on metal content). Rare earth metal content between about 1 and 8%w is preferred, and between about 2 and 4%w is most preferred. The amount of the one or more alkali or alkaline earth metals, if used to promote catalyst performance is suitably between about 0.01 and 4%w, based on carrier, preferably between about 0.01 and 1.0%w, and most preferably between about 0.1 and 0.4%w. Similarly, the amount of the one or more transition metals, if present in the catalyst composition, is also suitably between about 0.1 and 4%w (based on carrier), preferably between about 0.01 and 1.0%w, and most preferably between about 0.1 and 0.4%w.

Catalysts suitable for the invention may be prepared by introducing the specified metals or compounds thereof onto the carrier by methods well known in the art, for example, by impregnation of the alumina support with aqueous solutions of soluble salts of the metals. Preferably, the catalyst is dried and calcined (e.g., at a temperature in the range from 450° to 625° C.) after a solution of metal nitrates or acetates has been adsorbed by the alumina. Calcination at higher temperature (e.g., 1100° C.) can then be conducted if reduction in surface area is desired.

The invention is further illustrated in the following Examples.

EXAMPLES I–VII

Catalysts containing didymium oxide $Di_2O_3$ (composition: 45.8%w $La_2O_3$, 9.5%w $Pr_6O_{11}$, 32.5%w $Nd_2O_3$, 5.5%w $Sm_2O_3$, 3.5%w $Gd_2O_3$, 0.5%w $Y_2O_3$, and 2.7%w other rare earth oxides) were prepared by impregnating a commercially available alpha-alumina carrier material (specific area 0.3 $M^2/g$; pore volume 0.2 ml/g; particle size 0.25–0.60 mm) with a solution of didymium nitrate in water, followed by drying at 120° C. for 178 hour and calcination at 500° C. for four hours.

For the practice of 3,5-xylenol preparation in accordance with one embodiment of the process of the invention, a sample of the catalyst (14.2 g; 12 ml) was placed in a microflow reactor. Pre-heated isophorone (purity about 97%) was passed over the catalyst at a temperature of 600° C., a pressure of 1 bar absolute, and varying space velocities. The conversion of isophorone and the selectivity to 3,5-xylenol were determined by gas-liquid chromatography.

For comparative purposes experiments were carried out, not in accordance with the invention. A catalyst without a rare earth component (Comparative Experiment A) and a catalyst according to British patent specification No. 1,451,570 (Comparative Experiments B and C) were tested under the same conditions. Also the thermal conversion of isophorone in the absence of any catalyst, was measured (Comparative Experiments D, E, F and G).

The results are shown in Table I, with conversion and selectivity expressed in molar percentages (%m) and space velocity in kilograms/liter of catalyst/hour (kg/l/hr). Catalyst metal content is in percentage by weight.

TABLE I

| Example | Catalyst | Space Velocity (kg/l/hr) | Conversion (% m) | Selectivity (% m) |
|---|---|---|---|---|
| I | 8.6% Di/αAl₂O₃ | 0.20 | 93 | 80 |
| II | 8.6% Di/αAl₂O₃ | 0.50 | 83 | 82 |
| III | 8.6% Di/αAl₂O₃ | 1.00 | 68 | 84 |
| IV | 4% Di/αAl₂O₃ | 0.25 | 93 | 79 |
| V | 4% Di/αAl₂O₃ | 0.50 | 80 | 79 |
| VI | 2% Di/αAl₂O₃ | 0.25 | 90 | 79 |
| VII | 2% Di/αAl₂O₃ | 0.50 | 74 | 75 |
| A | αAl₂O₃ | 0.30 | 40 | 68 |
| B | 4.2% CoO/10.8% MoO₃/ | 0.17 | 91 | 79 |
| C | 0.48% K on γ-Al₂O₃ | 0.33 | 79 | 75 |
| D | none | 0.07* | 82 | 60 |
| E | none | 0.14* | 70 | 61 |
| F | none | 0.35* | 50 | 54 |
| G | none | 0.70* | 34 | 46 |

*kg isophorone/l of empty reactor space at 590-610° C./hour.

EXAMPLE VIII–XXI

Catalysts suitable for use in accordance with the invention, comprising transition metals, were prepared as in the preceding Examples, except that the Al₂O₃-carrier material was impregnated with an aqueous solution of a transition metal nitrate as well. The reaction conditions were again 600° C. and 1 bar. The results are tabulated in Table II.

TABLE II

| Example | Catalyst | Space Velocity (kg/l/hr) | Conversion (% m) | Selectivity (% m) |
|---|---|---|---|---|
| VIII | 8% Di/0.8% Mo | 0.25 | 95 | 81 |
| IX | 8% Di/0.8% Mo | 0.50 | 82 | 79 |
| X | 8% Di/0.8% Mo | 1.00 | 76 | 80 |
| XI | 8% Di/0.4% Mo | 0.26 | 77 | 77 |
| XII | 8% Di/0.4% Mo | 0.53 | 76 | 77 |
| XIII | 8% Di/0.8% Co | 0.25 | 100 | 82 |
| XIV | 8% Di/0.8% Co | 0.45 | 99 | 80 |
| XV | 8% Di/0.8% Co | 0.92 | 85 | 85 |
| XVI | 4% Di/0.4% Cu | 0.25 | 93 | 80 |
| XVII | 4% Di/0.4% Cu | 0.50 | 73 | 70 |
| XVIII | 4% Di/0.4% Ag | 0.25 | 94 | 70 |
| XIX | 4% Di/0.4% Ag | 0.50 | 74 | 72 |
| XX | 4% Di/0.4% Co | 0.185 | 98 | 78 |
| XXI | 4% Di/0.4% Co | 0.46 | 98 | 75 |

Examples XXII–XXIII

Catalysts suitable for use in accordance with the invention comprising the alkali metal potassium, were prepared as in the first seven Examples, except that the Al₂O₃-carrier material was impregnated with an aqueous solution of potassium nitrate as well. The reaction conditions were again 600° C. and 1 bar. The results are tabulated in Table III.

TABLE III

| Example | Catalyst 4% Di/ | Space Velocity (kg/l/hr) | Conversion (% m) | Selectivity (% m) |
|---|---|---|---|---|
| XXII | 4% Di/0.4% K | 0.50 | 100 | 80 |
| XXIII | 4% Di/0.4% K | 1.00 | 95 | 79 |

EXAMPLES XXIV–XXXII

Isophorone was converted to 3,5-xylenol in accordance with the invention using catalysts containing didymium, cobalt, and potassium. The preparation of the catalysts was analogous to the preceding Examples. Reaction conditions were again 600° C. and 1 bar. Results are shown in Table IV.

TABLE IV

| Example | Catalyst 4% Di/ | Space Velocity (kg/l/hr) | Conversion (% m) | Selectivity (% m) |
|---|---|---|---|---|
| XXIV | 0.1% Co/0.4% K | 0.50 | 100 | 85 |
| XXV | 0.1% Co/0.4% K | 1.00 | 95 | 85 |
| XXVI | 0.4% Co/0.4% K | 0.50 | 99 | 80 |
| XXVII | 0.4% Co/0.4% K | 1.00 | 97 | 80 |
| XXVIII | 0.4% Co/0.8% K | 0.50 | 100 | 79 |
| XXIX | 0.4% Co/0.8% K | 1.00 | 95 | 81 |
| XXX | 0.4% Co/0.1% K | 0.50 | 100 | 81 |
| XXXI | 0.1% Co/0.1% K | 0.50 | 99 | 85 |
| XXXII | 0.1% Co/0.1% K | 1.00 | 98 | 83 |

EXAMPLES XXXIII–XXXVI

These Examples show the effect of different temperatures and space velocities on practice of the invention using preferred catalysts. The results are shown in Table V which also includes the results obtained in Examples XXX and XXXI and Comparative Experiments B, H and J, which Comparative Examples make use of the catalyst described in British patent specification No. 1,451,570. Examples XXXIII and XXXIV use the same catalyst as Example XXX; Examples XXXV and XXXVI use the same catalyst as Example XXXI.

TABLE V

| Example | Catalyst | Space Velocity (kg/l/hr) | Conversion (% m) | Selectivity (% m) | Temperature (°C.) |
|---|---|---|---|---|---|
| XXX | See Table IV | 0.50 | 100 | 81 | 600 |
| XXXIII | " | 0.50 | 61 | 82 | 550 |
| XXXIV | " | 0.25 | 94 | 82 | 550 |
| XXXI | See Table IV | 0.50 | 99 | 85 | 600 |
| XXXV | " | 0.50 | 71 | 82 | 550 |
| XXXVI | " | 0.67 | 99 | 80 | 630 |
| B | See Table I | 0.17 | 91 | 79 | 600 |
| H | " | 0.25 | 62 | 77 | 550 |
| J | " | 0.25 | 23 | 60 | 500 |

We claim as our invention:

1. A process for the preparation of 3,5-xylenol from isophorone which comprises contacting isophorone at a temperature in the range from about 525° to 625° C. with a heterogeneous catalyst comprising didymium supported on an alumina carrier, said catalyst containing between about 0.5 and 20 percent by weight of didymium, calculated on weight of the carrier.

2. The process of claim 1, wherein the catalyst contains between about one and 8 percent by weight of didymium, and the catalyst has a surface area less than about 0.5 square meter per gram.

3. The process of claim 2, wherein the carrier is an alpha-alumina.

4. The process of claim 3, wherein the catalyst contains between about 2 and 4 percent by weight of didymium.

5. A process for the preparation of 3,5-xylenol from isophorone which comprises contacting isophorone at a temperature in the range from about 525° C. to 625° C. with a heterogeneous catalyst comprising between about 0.5 to 20 percent by weight of didymium and between about 0.01 and 4.0 percent by weight of one or more alkali or alkaline earth metals supported on an alumina carrier, said catalyst having a surface area not exceeding about 1.0 square meter per gram.

6. The process of claim 5, wherein the catalyst contains between about one and 8 percent by weight of didymium, and the catalyst has a surface area less than about 0.5 square meter per gram.

7. The process of claim 6, wherein the catalyst contains between about 0.01 and 1.0 percent by weight of the one or more alkali or alkaline earth metals.

8. The process of claim 7, wherein the carrier is an alpha-alumina.

9. The process of claim 8, wherein the catalyst contains potassium in an amount between about 0.01 and 1.0 percent by weight.

10. The process of claim 7, wherein the catalyst contains between about one and 8 percent by weight of didymium.

11. The process of claim 9 wherein the catalyst contains between about one and 8 percent by weight of didymium.

12. A process for the preparation of 3,5-xylenol which comprises contacting isophorone at a temperature in the range from about 525° to 625° C. with a heterogeneous catalyst comprising between about 0.5 and 20 percent by weight of didymium and between about 0.01 and 4.0 percent by weight of one or more transition metals in Groups IB, VIB, and VIII of the Periodic Table supported on an alumina carrier, said catalyst having a surface area not exceeding about 1.0 square meter per gram.

13. The process of claim 12, wherein the catalyst contains between about one and 8 percent by weight of didymium, and the catalyst has a surface area less than about 0.5 square meter per gram.

14. The process of claim 13, wherein the catalyst contains between between about 0.01 and 1.0 percent by weight of the one or more transition metals.

15. The process of claim 14, wherein the carrier is an alpha-alumina.

16. The process of claim 15, wherein the catalyst contains cobalt in an amount between about 0.01 and 1.0 percent by weight.

17. The process of claim 14, wherein the catalyst contains between about one and 8 percent by weight of didymium.

18. The process of claim 16, wherein the catalyst contains between about one and 8 percent by weight of didymium.

19. The process of claim 12, wherein the catalyst additionally comprises between about 0.01 and 4.0 percent by weight of one or more alkali or alkaline earth metals supported on the alumina carrier.

20. The process of claim 19, wherein the catalyst contains between about one and 8 percent by weight of didymium, and the catalyst has a surface area less than about 0.5 square meter per gram.

21. The process of claim 20, wherein the catalyst contains between about 0.01 and 1.0 percent by weight of the one or more transition metals and between about 0.01 and 1.0 percent by weight of the one or more alkali or alkaline earth metals.

22. The process of claim 21, wherein the carrier is an alpha alumina.

23. The process of claim 22, wherein the catalyst contains cobalt in an amount between about 0.01 and 1.0 percent by weight and potassium in an amount between about 0.01 and 1.0 percent by weight.

24. The process of claim 21, wherein the catalyst contains between about one and 8 percent by weight of didymium.

25. The process of claim 23, wherein the catalyst contains between about one and 8 percent by weight of didymium.

26. The process of claim 25, wherein the catalyst contains about 4 percent by weight of didymium, between about 0.1 and 0.4 percent by weight of potassium, and about 0.1 percent by weight cobalt, supported on an alpha-alumina carrier.

* * * * *

UNITED STATES PATENT AND TRADEMARK OFFICE
CERTIFICATE OF CORRECTION

PATENT NO. : 4,453,025
DATED : June 5, 1984
INVENTOR(S) : Antonius J. C. Van Seters; Freddy Wattimena It is certified that error appears in the above-identified patent and that said Letters Patent are hereby corrected as shown below:

In the listing of References Cited, Foreign Patent Documents, the United Kingdom documents numbered 1,190,802, 1,190,803 and 1,190,804 should read 1,197,802, 1,197,803 and 1,197,804, respectively.

Signed and Sealed this

Twenty-sixth Day of March 1985

[SEAL]

Attest:

DONALD J. QUIGG

Attesting Officer     Acting Commissioner of Patents and Trademarks